United States Patent [19]

Neumann

[11] 4,086,331
[45] Apr. 25, 1978

[54] GELATIN-BASED COMPOSITIONS AND A METHOD FOR THE GENERATION OF STABILIZED FOAMS THEREFROM

[75] Inventor: Peter Neumann, Haifa, Israel

[73] Assignee: Technion Research and Development Foundation Ltd., Haifa, Israel

[21] Appl. No.: 697,258

[22] Filed: Jun. 17, 1976

[30] Foreign Application Priority Data

Jan. 7, 1975 Israel .......................................... 74615

[51] Int. Cl.² .......................... A61L 9/04; B01J 13/00
[52] U.S. Cl. ................................... 424/45; 21/60.5 A; 47/2; 71/64 G; 252/3; 252/8.05; 252/307; 424/177; 424/340; 424/360; 424/DIG. 13
[58] Field of Search .......................... 252/307, 3, 8.05; 424/45, 177, DIG. 13

[56] References Cited

U.S. PATENT DOCUMENTS

| | | | |
|---|---|---|---|
| 1,423,719 | 7/1922 | Jennings | 252/307 |
| 1,856,294 | 5/1932 | Rice | 252/307 |
| 2,801,201 | 7/1957 | Kipnis | 424/45 |
| 3,186,943 | 6/1935 | Barthauer | 252/3 X |
| 3,198,702 | 8/1965 | Hellbaum | 424/DIG. 13 |
| 3,325,366 | 6/1967 | Blaug et al. | 424/45 X |
| 3,475,333 | 10/1969 | Meldrum et al. | 252/307 X |
| 3,664,965 | 5/1972 | Hirota et al. | 252/307 X |

OTHER PUBLICATIONS

British Pharmacopoeia, 1973, p. 104.
Merck Index, 8th Edition, p. 249.

*Primary Examiner*—Richard D. Lovering
*Attorney, Agent, or Firm*—Browdy and Neimark

[57] ABSTRACT

A method for the generation of gelatin-based stabilized foams by passing a stream of air or other gas through a composition of the gelatin, an anionic surface-active agent and a water soluble ferrous salt. The resulting foams have a relatively long life term.

15 Claims, No Drawings

GELATIN-BASED COMPOSITIONS AND A METHOD FOR THE GENERATION OF STABILIZED FOAMS THEREFROM

FIELD OF THE INVENTION

The present invention relates to new compositions of gelatin-based solutions and to a method for the preparation of foams therefrom. More particularly, the invention relates to a method for the preparation of new gelatin-based foams having a relatively long life-time.

BACKGROUND OF THE INVENTION

As is known, foams consist of bubbles of gas whose walls are thin liquid films. Pure liquids do not foam, and short-lived aqueous foams can be generated by passing a stream of air through a solution containing a surface active agent.

Foams per se are thermodynamically unstable since their collapse is accompanied by a decrease in the total free energy. The addition of a polymer may extend the life-time of such foams by several hours. However, since such foams remain in liquid form, their life-time is generally limited by:

(a) The tendency of water to evaporate from the liquid surface to the air, and (b) The tendency of liquid to drain from the bubble walls.

These factors lead to a gradual thinning and weakening of the bubble wall until it is no longer themodynamically stable and bursts, i.e. the life-time of the foam is governed by the rate at which water drains or evaporates from the walls of the bubbles.

The addition of preformed polymer is beneficial in increasing the viscosity of the foam solution and thus decreasing drainage and also increasing the water holding capacity of the foam. The properties of such foams, containing various stabilizers such as citrus pectin, starch phosphate and gelatin used in a range of concentrations between 1 to 2% are discussed in an article which appeared in Transactions of the American Society of Agricultural Engineers, Vol. 13, No. 1, pp 1-5 (1970). In addition to the stabilizer, small amounts of binding agents such as $CaHPO_4$ or glycerol are utilized. As pointed out in the article, mixtures with less than 1% gelatin had little skin-forming ability and were thus not recommended as long-life foams. The foams described in the article were suitable for plant protection, provided that the surrounding temperature was below 5° C; at higher temperatures the foam collapsed.

The yield of foams may be expressed by the expansion factor. For several agricultural applications, e.g. plant protection, the expansion factor should be as high as possible for maximum economy. The expansion factor is defined as the reciprocal of the density. According to the article mentioned above, the foams stabilized with gelatin had expansion factor between 35.3 to 55.

SUMMARY OF THE INVENTION

It is the object of the present invention to describe new compositions of gelatin-based solutions, which can be used to generate foams possessing a relatively long life-time. It is another object of the present invention to describe new compositions of gelatin-based solutions which can generate foams at ambient temperature, said foams having a relatively long life-time.

DESCRIPTION OF PREFERRED EMBODIMENTS

The invention consists of compositions of gelatin-based solutions comprising between 0.1 to 3% by wt of gelatin and an anionic surface active agent, said compositions being characterized in that they contain between 0.1 to 1% by wt of a water soluble ferrous salt. The invention is based on the discovery that by the incorporation of small amounts of a water soluble ferrous salt into an aqueous solution containing gelatin, and an anionic surfactant, the gelatin-based foams obtained possess a relatively long life-time. The bubble diameter of the foams may be in a broad range of between about 1 mm to about 10 mm. depending on the method of foam generation. Foams obtained from the new compositions may thus have broad ranges of density between 0.35 and 20 g/100 cc i.e. expansion factors in the range of 5 to 280.

In contrast to all other foams generated from aqueous gelatin solutions, the foams obtained from the compositions according to the present invention, set into relatively rigid stabilized foams as they dry.

The nature of the mechanism which will explain the beneficial effect of the ferrous salt on the stability of the foam is complex and not yet fully understood. A reasonable assumption is that the incorporation of the ferrous salt causes an unexpected increase of the surface viscosity and in so doing reduces drainage and gas permeability. It seems that upon aeration and formation of the foam, an interaction occurs between the ferrous ions and gelatin. This interaction involves the oxidation of the ferrous ions to ferric ions and may cause a redistribution of the water in the hydration shell of the gelatin. At the same time an increase in the electrostatic forces occurs which act to precipitate the gelatin out of solution. As a result of this precipitation, a stable film consisting of a network of precipitated gelatin replaces the unstable aqueous film. This explanation seems to be reasonable but of course other theories may be suggested; however, these are beyond the scope of the present specification. Generation of foams using the compositions according to the present invention can be carried out by normal methods of foam formation, even at ambient temperature. Generally the preferred temperature at which the foams are generated, is in a range of between 5° C to about 30° C. By using compositions which have been previously cooled, higher viscosity solutions can be obtained, and thus stronger foams result.

The new gelatin-based compositions have an important advantage from the economical point of view since very dilute gelatin concentrations can be used, generally in the range of 0.1 to 3% by wt, the optimal concentration depending on the specific use. All types of gelatin can be used, where those of higher quality, i.e. those with a higher molecular weight, can be used at relatively lower concentrations. The choice of quality and concentration will be governed by economical considerations. Any person skilled in the art will certainly know how to select the proper gelatin according to the specific use.

Any anionic surfactant such as water-soluble salts of long-chain carboxylic acids, sulfonates such as dodecyl benzene sulfonate, dialkyl esters of sodium sulfosuccinic acid may be used in the compositions; particularly preferable are fluorocarbon surfactants. The fluorocarbon surfactants form surfaces of much lower free-energy than hydrocarbon surfaces and consequently lower the surface tension of the solution to a greater extent than hydrocarbon surfactants. Example of a fluorocarbon surfactant is FC 128; (Trade Mark produced by 3M Company). Concentrations of surfactant in the range between about 0.01% to about 0.2% by wt as normally used in foam generation, can be utilized also in the compositions according to the present invention.

The incorporation of a water-soluble ferrous salt in the gelatin-based compositions for foam generation is the crux of the present invention. Among various water soluble ferrous salts which can be utilized the following can be mentioned: ferrous sulphate, ferrous acetate, ferrous bromide, ferrous nitrate, ferrous chloride etc.; preferred salts which give the best results are the commonly available ferrous sulphate and ferrous chloride. The concentration of the ferrous salt should not surpass 1% by wt of the composition and should preferably be in the range of 200 to 800 ppm of iron.

The method of foam generation is the common method used, wherein air, an inert gas or mixtures thereof or a propellant are used as blowing agents. The physical properties of the gelatin film in the bubble walls can be predetermined conveniently by adding small amounts of a polyhydric alcohol or sugar to the composition before generating the foam. In this manner more flexible or more rigid foams may be produced.

The new gelatin-based foams obtained according to the present invention can be used in a broad range of uses such as: protecting plants against cold weather or hot dry winds, fire extinguishing, soil sterilization, temporary storage of toxic gases, as carrier for micronutrients in fertilizer or as carrier for pesticides.

When used as a fire extinguishing or prevention agent, the foams can be generated by blowing with an inert gas such as nitrogen.

In crop fertilization the presence of increased concentration of $CO_2$ is sometimes beneficial to growth of certain plants. According to the present invention the foams could be generated with a $CO_2$-enriched air, so that the $CO_2$ could provide the plant requirement. Thus no additional structure for the introduction of $CO_2$ will be necessary.

In medical use the foams can be utilized for treatment of human burn wounds. Various bactericides can be incorporated into the solution in order to preserve the foam-generation solution and also to enhance the medical usefulness. Such foams can also be generated in enclosed aerosol containers when formulated with a suitable propellant. These foams may also be utilized as retardants of water evaporation in lakes or as temporary heat insulating matter. Of course any person skilled in the art, appreciating the improved properties of the foams obtained with the new compositions according to the present invention, could also envisage other areas of utilization. For example, by incorporating into the above compositions a polyol such as glycol or glycerine the foams obtained will collapse slowly into a composite film.

One of the advantages of the foams obtained according to the present invention, is that all the components present in the compositions are relatively cheap, non-toxic and thus not detrimental in their use to plants or other biological system.

According to another embodiment of the present invention, the composition may contain in addition to water, a surfactant, gelatin and the ferrous salt, a water-miscible organic solvent which does not dissolve the protein substratum of the gelatin. In this way the foam will dry faster than without the incorporation of the organic solvent. Examples of such organic solvents are methanol, ethanol, propanol, etc. The amount of the organic solvent is generally in the range between about 1% to 15% by wt. Such compositions which contain a water miscible organic solvent will be particularly useful for instant burn treatment where a rapid rate of drying in order to obtain the rigid foam is requisite. The fast evaporation of such foams is accompanied by a rapid cooling effect which is beneficial in the first aid treatment.

According to still another embodiment of the present invention it is also possible to incorporate into the composition small amounts (in the range of 0.01% to 0.4% by wt) of an aldehyde such as formaldehyde or glutaraldehyde, which will cause cross-linking with the gelatin and thus strengthen the foam. It was surprisingly found that this cross-linking can stop the gelation of dilute solutions of gelatin at low temperatures. Such cross-linked foam solutions are characterized by their ability to remain in liquid state even after prolonged storage at low temperatures. This property is very useful in medical applications when a strong type of foam obtained by an aerating of a precooled foam-generating solution is desirable. Conventional gelatin-based solutions at concentrations above 0.7% by wt. will gel at low temperatures and cannot therefore immediately be aerated to produce foams.

A further embodiment of the present invention is the incorporation into the compositions of various fillers such as cellulose fibers or glass beads according to the specific requirement. For example, when cellulose fibers are incorporated into the composition, a product similar to an expanded mat will be obtained. This can also find use in medical application due to its greater capability to absorb fluids.

In the following Table are summarized the advantages of the foams obtained according to the present invention, as compared with the conventional gelatin-based foams used for frost protection:

| Property | Conventional gelatin-based foam | Gelatin-based foam, according to the present invention |
|---|---|---|
| Temperature for foam generation | Above 30° C | 5 to 40° C |
| Range of temperature stability of foam | −15° to 5° C | −15° to 50° C |
| Minimum gelatin content for stability | 1 to 2% | 0.2 to 0.6% |
| Maximum expansion factor (allowing stability to winds) | 35 – 55 | Above 150 |

The above comparative results clearly show the advantages of the foams obtained according to the present invention as compared with conventional gelatin-based foams.

In order to further and fully illustrate the nature of this invention and the manner of practicing it, the following examples are presented for clearness of understanding only, and no limitation should be understood therefrom.

EXAMPLE 1

A solution is prepared by dissolving 6 g. of gelatin, 3 g. of ferrous sulphate (Fe $SO_4.7H_2O$) and 1 g. of surfactant (FC 128, trade mark produced by 3M Company) in one liter of distilled water. By passing, at ambient temperature (25° C), a stream of air through orifices of 1 mm diameter, a foam with about 1 cm diameter bubbles is obtained. The foam becomes rigid about ten minutes after generation and is stable for several days. The density of the wet foam is 0.37 g/100 cc which means that the expansion factor is 270. When this foam was applied to potted plants, they were relatively unaffected either by a treatment for one hour at $-15°$ C or by the foam itself, as judged by their subsequent growth over a 7-day period. The foam was also applied to seedlings which were transferred to a forced draught drying oven at 40° C for a 24-hour period. After 24 hours all of the unprotected seedlings had withered, whereas the foam covered plants were erect and subsequently grew through the protective foam layer.

EXAMPLE 2

The previous experiment was repeated using 2 g of ferrous chloride ($FeCl_2.4H_2O$) instead of ferrous sulphate and sodium lauryl sulphate (2 g) instead of FC 128. The amounts of other materials used were the same as those previously mentioned. The foams obtained had the same stable property as those obtained with ferrous sulphate.

EXAMPLE 3

A solution was obtained by dissolving 6 g. of gelatin, 3 g. of ferrous sulphate ($FeSO_4 \cdot 7H_2O$), 0.5 g. of surfactant (FC 128) and 90 ml ethanol (96%) in 910 ml of distilled water. Air was passed at ambient temperature (25° C) through a sintered glass disc into the above solution. The foam obtained had an initial rate of drying 100% faster than that of a foam obtained from a similar solution without ethanol.

EXAMPLE 4

Experiment 3 was repeated, incorporating into the solution 1 g. of "Geocophen" (Trade mark produced by BDH, England) which is a broad range biocide. The incorporated additive did not affect the ability of generating the stable foam.

EXAMPLE 5

A solution was prepared by dissolving together the following:
10 g gelatin
3 g ferrous sulphate ($FeSO_4.7H_2O$)
0.5 g surfactant (FC 128)
90 ml ethanol (96%)
8 ml of glutaraldehyde (25%) and
912 ml water The solution was stored in a refrigerator at 7° C for three days. After that the solution was aerated immediately, the foam obtained being stable as in Example 3. A comparative experiment without the incorporation of glutaraldehyde showed that the solution from the refrigerator gelled and could not be foamed immediately.

EXAMPLE 6

A foam was generated as in Example 3, but instead of 90 ml of ethanol, an amount of 20 ml glycerine was incorporated into the solution. The foam obtained collapsed after several hours and a thick composite film resulted.

It will be obvious to those skilled in the art that various changes may be made without departing from the scope of the invention and the invention is not to be considered limited to what is described in the specification.

What is claimed is:

1. A composition suitable for use in medicine and agriculture for the treating of burns or the coating of plants by the application thereto of a stable gelatin-based foam, comprising
an aqueous solution of 0.1 to 3% by weight of gelatin; 0.01 to 0.2% by weight of an anionic surface active agent; an amount sufficient to stabilize said gelatin-based foam up to 1% by weight of a water soluble ferrous salt; and an amount sufficient of glutaraldehyde to maintain said composition in liquid state even after prolonged storage at low temperatures; said composition being non-toxic.

2. A composition according to claim 1, wherein the water soluble ferrous salt is ferrous sulfate or ferrous chloride.

3. A composition according to claim 1, wherein the amount of iron incorporated is in the range of 200 to 800 ppm.

4. A composition according to claim 1, wherein the anionic surface active agent is selected from the group consisting of water-soluble salts of long-chain carboxylic acids, sulfonates and fluorocarbon surfactants.

5. A composition according to claim 1, wherein 1-15% by weight of a water-miscible organic solvent is incorporated into the composition.

6. A composition according to claim 5, wherein the water-miscible organic solvent is selected from the group consisting of methanol, ethanol n-propanol and isopropanol.

7. A composition according to claim 1, wherein an amount sufficient to cause a slow collapse of foam of a polyol selected from the groups consisting of glycol and glycerine is incorporated into the composition.

8. A composition in accordance with claim 1, wherein said glutaraldehyde is present in an amount of 0.01 to 0.4% by weight.

9. A medicinal composition in accordance with claim 8, wherein said composition further contains an amount sufficient, to enhance evaporation of the water from said aqueous solution, of a water-miscible organic solvent selected from the group consisting of methanol, ethanol, n-propanol and isopropanol; and a bacterialcidal-effective amount of a bacteriacide.

10. An aerosol package for a generating gelatin-based foam for medical application comprising an aerosol container formulated with a suitable propellant and containing the composition of claim 9.

11. A method of treating burns comprising foaming the composition of claim 1 and applying said foam to the burned skin surface at a temperature of 5°– 30° C.

12. A method according to claim 11, wherein an amount sufficient to cause a slow collapse of foam of a polyol selected from the group consisting of glycol and glycerine is incorporated into the compositions prior to foaming.

13. A gelatin-based foam made by the method according to claim 11, having an expansion factor in the range of 5 to 280.

14. A method of treating burns comprising foaming the composition of claim 9 and applying said foam to the burned skin surface at a temperature of 5°– 30° C.

15. A gelatin-based foam applied as a surface coating to the skin, said foam being made by the method of claim 14 and having an expansion factor of 5 to 280.

* * * * *